US00PP09536P

United States Patent [19]

Meilland

[11] Patent Number: Plant 9,536

[45] Date of Patent: May 7, 1996

[54] SHRUB ROSE PLANT NAMED 'MEICHONAR'

[75] Inventor: Alain A. Meilland, Antibes, France

[73] Assignee: The Conard-Pyle Company, West Grove, Pa.

[21] Appl. No.: 492,209

[22] Filed: Jun. 19, 1995

[51] Int. Cl.[6] ..... A01H 5/00

[52] U.S. Cl. ..... Plt./1

[58] Field of Search ..... Plt./1, 22, 23

*Primary Examiner*—Howard J. Locker

*Attorney, Agent, or Firm*—Burns, Doane, Swecker & Mathis

[57] ABSTRACT

A new and distinct variety of shrub rose plant is provided which forms continuously throughout the season attractive long-lasting White blossoms that are more or less edged with Venetian Pink. The new variety grows well on its own roots and forms relatively few thorns (as illustrated). The plant possesses a bushy growth habit. Also, the new variety exhibits very good disease resistance, as is well suited for use as attractive ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was the product of the artificial pollination of the 'Meidomonac' variety U.S. Plant Pat. No. 5,105) and the 'Pascali' variety U.S. Plant Pat. No. 2,592). The male parent (i.e., the pollen parent) of the new variety was the 'Edelweiss' variety (non-patented in the United States). The parentage of the new variety can be summarized as follows:

('Meidomonac'×'Pascali')x'Edelweiss'.

The seeds resulting from the above pollination were sown and 11 small plants were obtained which were physically and biologically different from each other. Selective study resulted in the identification of a single plant of the new variety.

It is found that the new variety of shrub rose plant possesses the following combination of characteristics:

(a) forms continuously throughout the season attractive blossoms which are White and more or less edged with Venetian Pink, (b) grows well on its own roots, (c) forms few thorns, (d) is particularly well suited for growing in the landscape, and (e) exhibits very good disease resistance.

The new variety exhibits good growth characteristics when grown on its own roots in alkaline soil.

The new variety meets the needs of the horticultural industry and can be grown to particular advantage as attractive ornamentation in parks, gardens, public areas, and residential landscapes.

The new variety of the present invention has been found to undergo asexual propagation by a number of routes in France including budding, grafting and cuttings. Asexual propagation by the above-mentioned routes as performed in France has shown that the characteristics of the new variety are homogeneous and stable and are strictly transmissible from one generation to another.

The new variety has been named the 'Meichonar' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during June while growing on their own roots outdoors at Le Cannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds as the sepals begin to open;

FIG. 4 — illustrates a specimen of a floral bud as the petals begin to open;

FIG. 5 — illustrates a specimen of a flower in the course of blooming;

FIG. 6 — illistrates a specimen of a open flower — plan view— obverse;

FIG. 7 — illustrates a specimen of a fully open flower — plan view— obverse;

FIG. 8 — illistrates a specimen of four fruits;

FIG. 9 — illustrates a specimen of a floral receptacle showing the arrangement of the stamens and pistils;

FIG. 10 — illustrates a specimen of a flowering stem;

FIG. 11 — illustrates a specimen of a main branch;

FIG. 12 — illustrates specimens of leaves with three leaflets— upper (left) and under (right) surfaces;

FIG. 13 — illustrates specimens of leaves with seven leaflets — upper (at bottom) and under (at top) surfaces; and FIG. 14 — illustrates specimens of leaves with five leaflets — plan view — upper (right) and under (left surfaces.

DETAILED DESCRIPTION

Figures 1, 2, 3, 4, 5, 6, 7, 8, 9, 10, 11, 12, 13, 14:
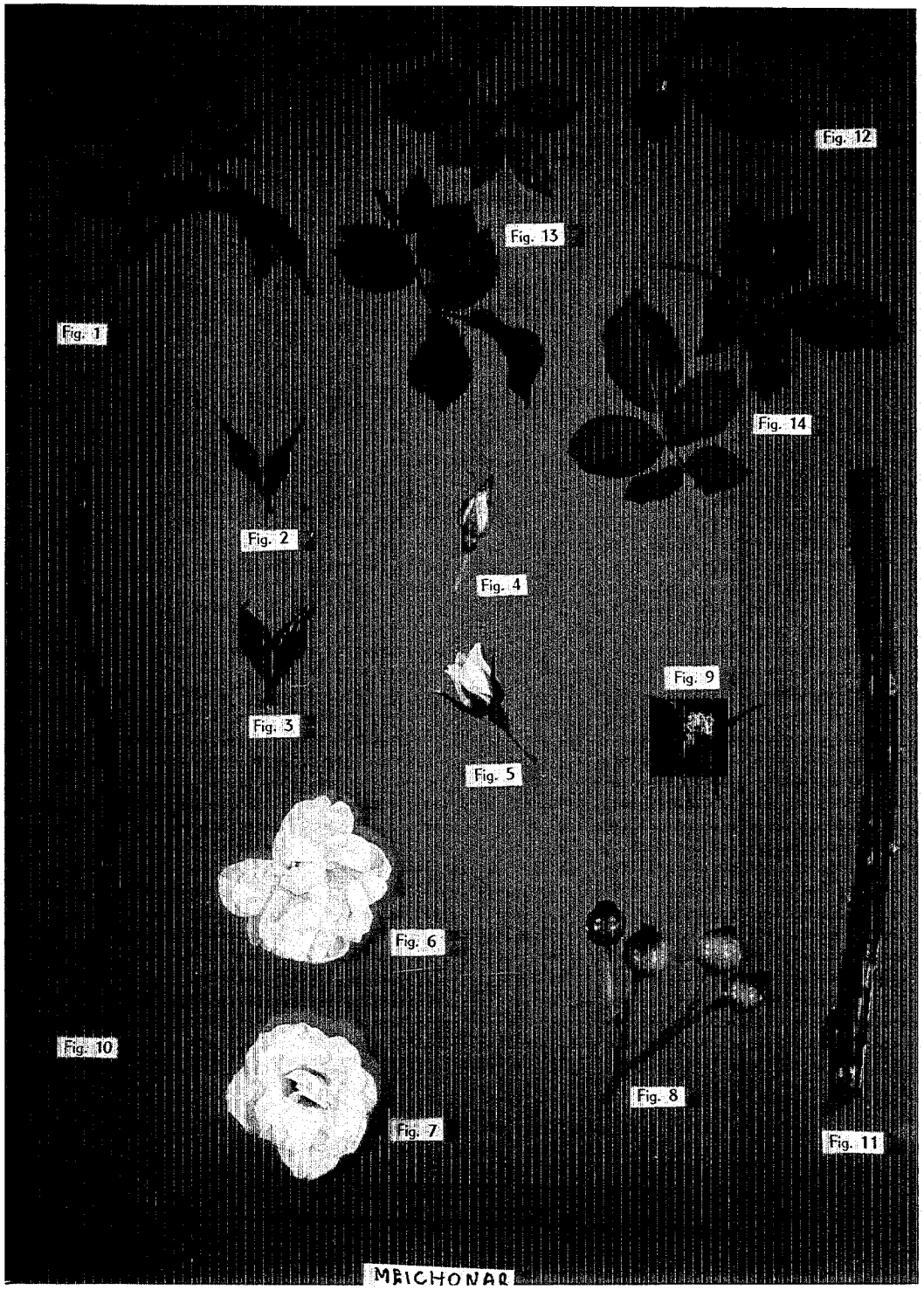

The chart used in the identification of the colors is that of The Royal Horticultural Society (R.H.S. Colour Chart). The terminology preceding the numbered reference to the chart has been added to indicate in more common terms the corresponding color. The description is based on the observation of two year-old specimens of the new variety while grown outdoors on their own roots during June at Le Cannet des Maures, Var, France.

Class: Shrub

Plant:

*Height.*—Approximately 130 cm. on average at the end of the growing season.

*Habit.*—Bushy.

Branches:

*Color.*—young stems: light green, Yellow-Green Group 144B. Adult wood: light green, Green Group 143C.

*Thorns.*—Size: small to medium. Quantity: very few ion adult wood. Color: pinkish to Havana brown.

Leaves:

*Stiples.*—adnate, pectinate, narrow and linear.

*Petioles.*—Upper surface: more or less glandular. Under surface: numerous prickles.

*Leaflets.*—Number: 3, 5, and 7. Shape: elliptic. Serration: as illustrated. Texture: coriaceous. General appearance: dense, normal green and semi-dull foliage. Color (young foliage): Upper surface: light green, Green Group 143B and more or less edged and suffused with reddish brown. Under surface: light green, Green Group 143C and widely suffused with reddish brown. Color (adult foliage): Upper Surface: medium green, Green Group 137A. Under surface: light brown, Green Group 137D.

Inflorescence:

*Number of flowers.*—Approximately 6 to 15 flowers per stem.

*Peduncle.*—Light green with numerous reddish glands, and approximately 2 to 2.5 cm. in length on average.

*Sepals*—Upper surface: tomentose, and greenish in coloration. Under surface: more or less glandular with few extensions.

*Buds.*—Shape: conical. Length: approximately 2 cm. on average. Size: medium for this rose class. Color when opening: Upper surface: White, White Group 155B, and more or less edged with Venetian Pink, Red Group 49C. Under surface: White, White Group 155B, and more or less edged with Venetian Pink, Red Group 49C.

*Flower.*—Form: cup-shaped. Diameter: approximately 6 cm. on average. Color (when opening begins): Upper surface: White, White Group 155B, and more or less edged with Venetian Pink, Red Group 49C. Under surface: White White Group 155B, and more or less edged with Venetian Pink, Red Group 49C. Color (when blooming): Upper surface: White, White Group 155B, and more or less edged with Venetian Pink, Red Group 49C. Under surface: White, White Group 155B, and more or less edged with Venetian Pink, Red Group 49C. Color (at end of opening): Upper surface: White, White Group 155B. Under surface: White; White Group 155B. Fragrance: none. Lasting Quality: long. Petal form: ovoid. Petal number: approximately 18 on average. Petal drop:L good. Stamen number: approximately 80 on average. Anthers: normal ochre coloration. Filaments: greenish in coloration and well arranged around the receptacle. Pistils: approximately 31 on average. Stigmas: strawlike-greenish in coloration. Styles: greenish and more or less twisted. Receptacle: medium green and smooth and in longitudinal section it is in the shape of a narrow pear.

Development:

*Vegetation.*—Strong.

*Blooming.*—Abundant and substantially continuous.

*Aptitude to bear fruits.*—Good.

*Resistance to diseases.*—Very good.

I claim:

1. A new and distinct variety of shrub rose plant characterized by the following combination of characteristics:

(a) forms continuously throughout the season attractive blossoms which are White and more or less edged with Venetian Pink, (b) grows well on its own roots, (c) forms few thorns, (d) is particularly well suited for growing in the landscape, and (e) exhibits very good disease resistance;

substantially as herein shown and described.

* * * * *

MEICHONAR